United States Patent [19]

Buchholz

[11] 4,203,807
[45] May 20, 1980

[54] ON-BOARD DETECTION OF ANTIKNOCK COMPOUNDS IN AUTOMOTIVE GASOLINE

[75] Inventor: Jeffrey C. Buchholz, Royal Oak, Mich.

[73] Assignee: General Motors Corporation, Detroit, Mich.

[21] Appl. No.: 22,337

[22] Filed: Mar. 20, 1979

[51] Int. Cl.² ............................................ G01N 27/26
[52] U.S. Cl. ................................ 204/1 T; 204/195 R; 324/439
[58] Field of Search .............. 204/1 T, 195 R; 324/29

[56] References Cited
U.S. PATENT DOCUMENTS

| | | | |
|---|---|---|---|
| 3,697,567 | 10/1972 | Taylor | 260/437 R |
| 3,960,690 | 6/1976 | Olson | 204/195 R |
| 4,012,290 | 3/1977 | Olson | 204/1 T |
| 4,012,291 | 3/1977 | Olson et al. | 204/1 T |
| 4,153,517 | 5/1979 | Olson | 204/1 T |

Primary Examiner—G. L. Kaplan
Attorney, Agent, or Firm—Douglas D. Fekete

[57] ABSTRACT

In the preferred embodiment, an electrochemical method of detecting the presence of tetraalkyl lead (or other organometallic antiknock additive) in an automotive gasoline sample comprises contacting the gasoline with an immiscible methanol solution containing KOH, which solution is the electrolyte of an electrochemical cell. The cell includes a stainless steel anode and a zinc cathode. Tetraalkyl lead is extracted from the sample into the methanol solution and metallic lead is deposited onto the zinc cathode. Thus, the lead deposit is evidence of the presence of tetraalkyl lead in the gasoline. The method is preferably adapted to be carried out on board a vehicle to monitor the fuel used therein.

Devices are presented which are adapted to be incorporated into the fuel tank or fuel line of a vehicle for detecting tetraalkyl lead by this method. In one embodiment, the detection device features a cathode comprising two closely spaced zinc surfaces. A predetermined amount of lead forms a continuous deposit between the zinc surfaces, which deposit is readily detected by a decrease in the electrical resistance between the zinc surfaces.

9 Claims, 3 Drawing Figures

ON-BOARD DETECTION OF ANTIKNOCK COMPOUNDS IN AUTOMOTIVE GASOLINE

BACKGROUND OF THE INVENTION

This invention relates to a method for detecting the presence of tetraalkyl lead compounds in automotive gasoline. More particularly, this invention relates to a method for detecting high concentrations of tetraalkyl lead compounds in gasoline, which method is readily carried out on board an automotive vehicle to determine the use of leaded gasoline therein.

It is well-known to improve the octane rating of automotive gasoline by the addition of a metal-containing organic compound such as tetraethyl lead, tetramethyl lead and methylcyclopentadienyl manganese tricarbonyl (MMT). In particular, gasoline containing tetraalkyl lead compounds is readily commercially available. For regular or leaded gasoline, the concentration of lead additives is typically about 0.4 g. Pb per liter. Even gasoline that is commercially designated "unleaded" generally contains a small concentration of lead compounds, typically 0.001 g. Pb per liter, and may permissibly contain as much as 0.013 g. Pb per liter. This invention is also applicable to MMT, which has recently been advanced as a substitute for the tetraalkyl lead compounds. However, the limited commercial use of MMT at this time makes it of secondary significance herein.

When leaded gasoline is used to operate an automotive vehicle that is equipped with a catalytic converter in the exhaust system for emission control purposes, lead-containing combustion products deposit onto the catalyst surfaces and impair their ability to oxidize exhaust hydrocarbons. As a result, the concentration of hydrocarbons in the emitted exhaust gas is substantially increased and may exceed automotive emissions standards. Catalyst performance is extremely sensitive to leaded gasoline use and even a short use, such as a single tankful, will essentially poison the catalyst. Furthermore, once poisoned, catalytic activity is not readily restored. Therefore, vehicles equipped with catalytic converters, require the use of unleaded gasoline only. However, leaded gasoline is occasionally introduced into the fuel supply and used to operate the vehicle, thereby poisoning the converter and increasing hydrocarbon emissions.

It would be advantageous to be able to determine whether the catalytic converter had been poisoned because the vehicle had been improperly operated with leaded gasoline. This determination may be made by monitoring the vehicle fuel to detect the presence of impermissibly high tetraalkyl lead concentrations. Because the gasoline composition in a vehicle periodically changes when additional fuel is introduced into the gas tank, detection would preferably be carried out on board the vehicle and provide a record for later examination. However, prior methods for detecting the tetraalkyl lead concentration involve sample pretreatment, carefully controlled conditions, time-consuming procedures and sensitive instruments. These methods are not readily adapted to be carried out on board a vehicle under typical automotive operating conditions.

Therefore, it is an object of this invention to provide a simple and versatile method and device for determining the concentration of tetraalkyl lead additives in an automotive gasoline sample. The method is performed directly on the gasoline sample without pretreatment and without significantly affecting the gasoline composition or its usefulness as automotive fuel. The method is also adaptable for detecting MMT or other organometallic additives in a gasoline sample. It is also an object of this invention to provide a method of detecting the presence of relatively high concentrations of tetraalkyl lead compounds in automotive gasoline, which method readily distinguishes commercial leaded and unleaded gasolines.

It is a further object of this invention to provide a method adapted to be carried out on board an automotive vehicle to monitor the fuel used therein to determine the amount of tetraalkyl lead compounds present in said fuel. The method of this invention is carried out under normal vehicle operating conditions by means of a portable, rugged device incorporated into the vehicle fuel supply. The method and device can detect if a predetermined significant amount of leaded additives has been used to operate the vehicle.

It is a still further object of this invention to provide a method and device for detecting whether too much leaded gasoline has been used in an automotive vehicle equipped with a catalytic converter of the type requiring the use of unleaded fuel. The method is capable of detecting if leaded gasoline is being used even if the usage is occasional and interspersed with larger quantities of unleaded gasoline.

It is also an object of this invention to provide an electrochemical method for detecting tetraalkyl lead compounds in gasoline, that produces a permanent record, in the form of a metallic lead deposit, which record may be examined by visual, electrical or other suitable means, to determine the amount of said compounds in the gasoline and, more particularly, if the total amount has been excessive. When the method is adapted to monitor a vehicle fuel supply over a prolonged period, the record (deposit) indicates any significant use of leaded gasoline to operate the vehicle requiring unleaded gasoline, which use may have occurred at any time prior to examination, whether or not leaded gasoline is present in the fuel supply at the time of examination.

It is also an object of this invention to provide an electrochemical device adapted to be incorporated into a fuel supply system on board an automotive vehicle to continually monitor the gasoline used therein to detect the presence of an impermissible amount of lead-containing additives, which amount corresponds to a significant use of leaded gasoline. The inexpensive device is of simple, but rugged construction and designed to function under normal vehicle operating conditions.

SUMMARY OF THE INVENTION

In a preferred embodiment, these and other objects are accomplished by bringing an automotive gasoline sample containing tetraalkyl lead additives into liquid-liquid extraction contact with an immiscible methanol electrolyte of an electrochemical cell having an anode and a cathode. It has been found that lead derived from the additives forms a metallic deposit on the cathode, thereby providing physical evidence of the presence of tetraalkyl lead in the sample.

The preferred electrolyte contains between about 0.25 to 2.5 weight percent potassium hydroxide KOH dissolved in methanol to improve electrical conductivity and also contains a small amount of water, at least 0.025 weight percent and preferably about 0.25 weight percent, sufficient to render the electrolyte substantially immiscible with the gasoline. The preferred lead-detecting cell also features a cathode comprising at least one metallic zinc surface and a stainless steel anode. An electrical potential of between about 1.7 to 3.0 volts is maintained between the cell electrodes. When the electrochemical cell is placed in contact with the gasoline sample for analysis, it is believed that tetraalkyl lead is extracted from the sample into the electrolyte and that the lead thus extracted is reduced at the cathode to form the elemental deposit. Thus, the size of the deposit is proportional to the additive concentration of the sample.

The amount of deposited lead may be determined by visual, gravimetric, electrical or other suitable analytical means. For example, the cell cathode may be a semibright zinc foil surface, in which case the lead forms a rough, dark deposit which is readily detectable by visual inspection. The size of the deposit is indicated by its color. A thin deposited film is light gray or brownish gray and is readily distinguished from the darker gray or black color associated with a larger deposit. Thus, for equivalent sample volumes, leaded gasoline forms a darker gray deposit that is readily perceived by the unaided eye and easily differentiated from the substantially lighter gray or grayish brown deposit formed by unleaded gasoline because of the lower additive concentration.

In the preferred embodiment, a deposit containing a predetermined amount of metallic lead is detected by electrical means. The cathode comprises two closely spaced zinc surfaces, preferably formed by two aligned segments of insulated zinc wire. Each segment has a substantially planar end substantially perpendicular to the wire longitudinal axis and comprising an exposed surface of the central zinc strand. The segments are aligned such that the exposed zinc surfaces lie immersed in the electrolyte in facing, parallel relationship, spaced apart by a predetermined distance. The segments are connected, at a point remote from the exposed end and preferably outside the cell, to an electrical resistance (ohm) meter to enable measurement of the resistance between the exposed zinc ends across the electrolyte. Prior to the deposition of any lead, the resistance has a first high value. When a lead-containing gasoline is placed in contact with the electrolyte, a dendritic or filamentary metallic lead deposit forms on each cathodically biased zinc wire end surface and grows generally in the direction of the opposite surface, causing the measured resistance to decrease. When a predetermined amount of lead has deposited, the deposit extends continuously between the zinc surfaces, resulting in a short circuit between the segments and causing the measured resistance to decrease to a second low value. The lead deposit required to decrease the resistance to the second low value depends upon the area of the zinc surfaces and the distance therebetween, among other factors. Thus, the resistance across the wire segments is evidence of the amount of the deposit and thereby indicative of the quantity of lead-containing compounds in the gasoline sample. The presence of an excessive lead deposit, such as that caused by the high tetraalkyl lead level in leaded gasoline, is demonstrated by the second low resistance.

Although the method and apparatus of this invention may be adapted for quantitative laboratory analysis of gasoline, it is primarily useful for distinguishing leaded from unleaded gasoline, particularly when carried out on board an automotive vehicle to monitor the fuel therein to detect a significant use of leaded gasoline. The electrochemical cell is readily incorporated into the vehicle gasoline tank or into the fuel line leading to the engine. Tetraalkyl lead in the gasoline is extracted into the KOH/water/methanol electrolyte and results in a permanent lead deposit accumulated on the cathode. The total lead accumulation depends upon the tetraalkyl lead concentration and the total sample volume. Therefore, the deposit integrates the vehicle tetraalkyl lead use and directly shows when the lead use has been sufficient to poison a catalytic converter. As a practical matter, only a minor accumulation is caused by unleaded gasoline having typically 0.001 g. Pb per liter concentration. By comparison, the cell rapidly deposits lead when exposed to leaded gasoline having a high tetraalkyl lead concentration about 400 times greater. Thus, a prior use of leaded gasoline in the vehicle may be readily determined by inspecting the cathode and comparing the accumulated deposit to a standard corresponding to the minor lead accumulation that would have been deposited had the vehicle been operated with only unleaded gasoline. An excessive deposit indicates a significant use of leaded gasoline. The cathode may be inspected by any suitable technique. In the preferred embodiment wherein the cathode comprises aligned zinc wire segments, the second low resistance value indicates an excessive deposit.

Thus, this invention provides a simple and versatile method for detecting relatively high concentrations of tetraalkyl lead in automotive gasoline and thereby distinguishing leaded from unleaded gasoline. The method is readily carried out on board an automotive vehicle, under normal operating conditions, by simply and directly placing the gasoline fuel in contact with the electrolyte of an electrochemical device, without sample pretreatment and without significantly affecting the sample composition. This invention provides a device of relatively simple, rugged construction adapted to be incorporated into a vehicle fuel supply system to monitor the gasoline used therein. The method and device of this invention is also adaptable to detecting MMT and other organometallic additives in automotive gasoline.

DETAILED DESCRIPTION OF THE INVENTION

Figure 1:
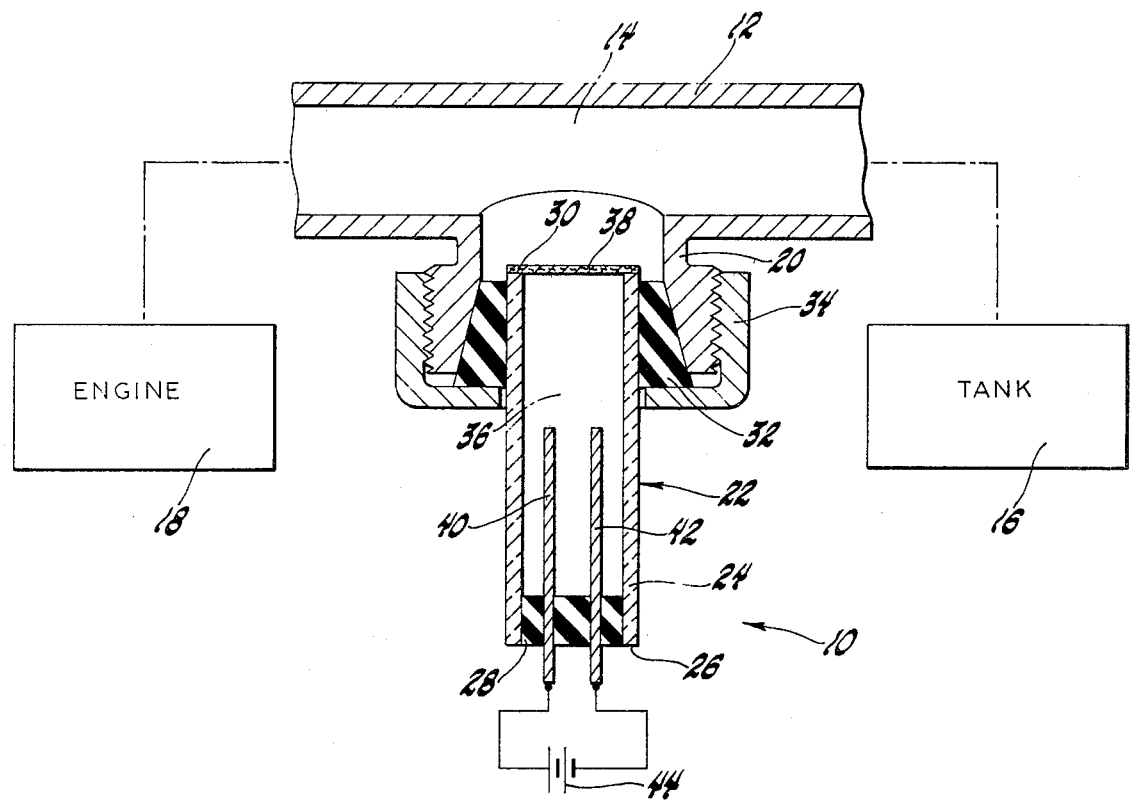
FIG. 1 is a cross-sectional view of a leaded gasoline detector of this invention incorporated into a vehicle fuel line and adapted for visual cathode inspection.

Referring to FIG. 1, there is presented an electrochemical detector 10 for carrying out the method of this invention on board an automotive vehicle to determine the use therein of leaded gasoline by visual examination. Detector 10 is incorporated into a fuel line 12 carrying gasoline 14 from a tank 16 to an engine 18 of the vehicle (not shown). Fuel line 12 is a horizontally oriented tubing formed of metal or other suitable material and provided with a downwardly extending, externally threaded cylindrical T-connection 20. Device 10 includes a vessel 22 constructed of a vertically oriented cylindrical glass tube 24 closed at lower end 26 by an epoxy plug 28 and coaxially fitted at open upper end 30 to T-connection 20. The approximately 1.2 cm. outer tube diameter, which is slightly less than the inner diameter of connection 20, enables a slight overlap to occur in the fitting therebetween. A fluid-tight seal is maintained between tube 24 and connection 20 by a polytetrafluoroethylene ring 32 and the fitting is threadably secured by nut 34. Connection 20, tube 24, ring 32 and nut 34 cooperate to form a swag lock or compression type coupling.

Vessel 22 has a length of approximately 7.6 cm. and an inner diameter of approximately 1.0 cm. Contained in vessel 22 is about 6 ml. of an electrolyte solution 36. Electrolyte 36 was initially prepared by dissolving about 0.2 g. KOH and about 0.1 ml. water in about 50 ml. absolute methanol. Obviously, commercial grade methanol containing water may be substituted for the absolute grade methanol employed in the example. A porous separator 38 comprising filter paper was mounted between electrolyte 36 and gasoline 14 to minimize turbulent mixing therebetween during typical vehicle operation. It is noted that the electrolyte is denser than gasoline so that the lower electrolyte phase is readily maintained within vessel 22.

Extending axially into vessel 22 through plug 28 is a stainless steel foil 40 and a zinc foil 42, each having dimensions within the vessel of about 5 mm.×25 mm.×0.1 mm. Zinc foil 42 had a shiny, smooth surface, characterized as semi-bright, but not specially polished. The portion of foils 40 and 42 within vessel 22 are surrounded by electrolyte 36 and are arranged substantially parallel, in facing relationship, and spaced apart by about 0.5 cm. Stainless steel foil is connected to the positive terminal of an external electrical D.C. power supply 44 to serve as the device anode and zinc foil 42 is connected to the negative terminal to serve as the cathode. A potential difference of about 2.0 volts is applied between the electrodes for lead detection.

During vehicle operation, gasoline 14 flows through fuel line 12. A portion contacts electrolyte 36 through porous separator 38. Tetraethyl lead or other organolead compounds contained in the gasoline are extracted into the electrolyte. The 2.0 volt applied potential between stainless steel anode 40 and zinc cathode 42 causes lead derived from the extracted compounds to form a metallic deposit on the surface of zinc cathode 42 facing anode 40. Under these conditions, the current required is typically less than 4 mA. In marked contrast to the shiny, smooth zinc surface, the resulting lead deposit is gray and rough and is clearly visible when the cathode is viewed through glass tubing 24.

In laboratory testing, Indolene Clear gasoline containing tetraethyl lead at a concentration of 0.4 g Pb per liter was flowed through fuel line 12 connected to device 10. After a short time, a gray-brown deposit was clearly visible on the surface of cathode 42 facing anode 40. The deposit grew progressively darker gray as gasoline flow continued. After five hours, an unmistakable, extremely dark gray deposit coated the cathode surface. It is estimated that unleaded gasoline containing 0.001 g. Pb per liter as organolead compounds would require at least 2,100 hours of gasoline flow to develop a similar dark gray coating. In terms of typical automobile use, device 10 is sensitive to detect the use of a single tankful of leaded gasoline during the course of 80,000 kilometers of driving.

Figure 2:
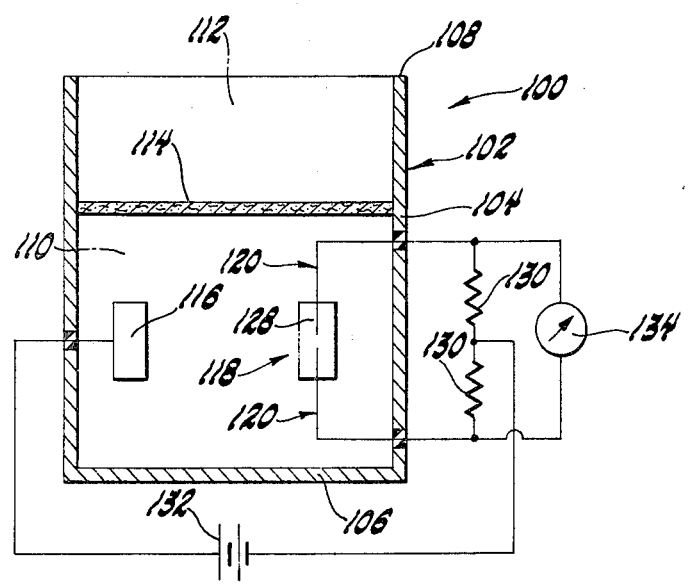
FIG. 2 is a cross-sectional view of an alternate leaded gasoline detector of this invention adapted to be incorporated into the fuel tank to provide an electrical measurement of the lead deposit.

Another embodiment of this invention is illustrated in FIG. 2. Detector 100 provides an electrical signal as a measure of the lead deposit. Detector 100 comprises a cup-shaped metallic vessel 102 having a cylindrical side wall 104 closed at the bottom by an integral end wall 106. Vessel 102 is secured inside a gas tank (not shown) of an automobile such that open top 108 lies below the gasoline surface. Vessel 102 is partially filled with an electrolyte 110 consisting of a water-containing methanol solution containing about 0.5 weight percent KOH. The remaining portion of vessel 102 above the electrolyte contains gasoline 112 from the tank reservoir. An advantage of partially filling vessel 102 with electrolyte is that spilling is minimized when the vehicle is operated upon uneven or bumpy surfaces. A porous separator 114 is mounted at the gasoline-electrolyte interface to further minimize turbulent mixing.

Figure 3:
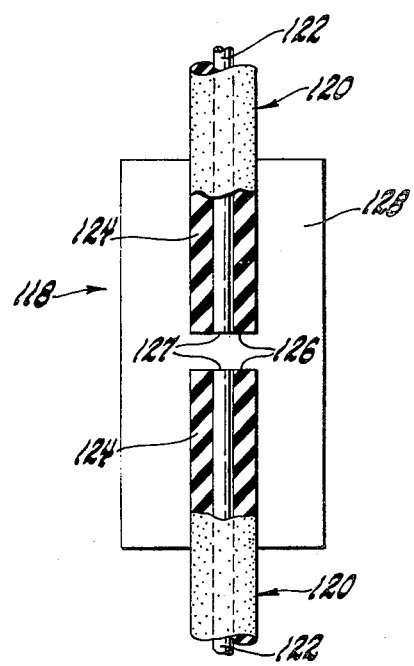
FIG. 3 in an enlarged view of the cathode construction of the detector presented in FIG. 2.

Suitably mounted within vessel 102 and immersed in electrolyte 110 are an anode 116 consisting of a stainless steel plate and a spaced cathode assembly 118. As seen better in FIG. 3, cathode assembly 118 comprises aligned insulated wire segments 120, each segment having a central metallic zinc wire strand 122 circumferentially enclosed in a polymeric insulating layer 124. Segments 120 have opposing end faces 126 which are generally perpendicular to the wire cylindrical axis. Thus, zinc strands 122 are exposed to electrolyte 110 only at surfaces 127 of end face 126. Segments 120 are mounted at the surface of an underlying supporting polymer (nonconductive) plate 128 such that end faces 126 of aligned segments 120 are in generally parallel, spaced relationship. Assembly 118 was readily constructed by partially embedding a portion of a single insulated zinc wire into the surface of an epoxy plate 128 and transversely cutting the embedded wire portion with a knife blade to form the two wire segments 120 having end faces 126 in the desired facing, spaced arrangement. In this embodiment, end faces 126 were spaced apart by a distance of about 25 microns.

Referring again to FIG. 2, cathode wire segments 120 are connected in parallel and through resistors 130 to the negative terminal of a remote DC electrical power supply 132. Thus, the negatively biased, exposed zinc surface 127 of each segment 120 is a cathode. Also segments 120 are connected to an electrical resistance (ohm) meter 134 to measure the resistance between segments 120, i.e., across electrolyte 110 between zinc surfaces 127. Resistors 130 are located outside the resistance-measuring circuit to prevent the circuit from being shorted. Anode 116 is suitably connected to the positive terminal of power source 132. A 2.0 volt DC potential is maintained between the anode and cathode.

Prior to the deposition of any metallic lead, the electrical resistance across segments 120 is very high, typically on the order of 100 kiloohms. Whenever electrolyte 110 is contacted by gasoline 112 containing tetraalkyl lead compounds, metallic lead is deposited onto cathodically biased zinc surfaces 127. The deposit comprises a plurality of filamentary or finger-like whiskers that grow on each surface 127 in the general direction of the opposite surface. As lead is initially deposited, the electrical resistance across the wire segments slowly decreases, until a sufficient amount of lead has accumulated to form a continuous filamentary deposit extending between surfaces 127. After a continuous deposit is formed, the deposition of addtional lead causes the resistance to decrease at a substantially greater rate in proportion to the rate of lead deposition. A large continuous lead accumulation may result in a measured resistance of less than 1,000 ohms, at which point the resistance is substantially unaffected by additional lead deposition. Thus, the electrical resistance measured across the cathode wire segments depends upon the amount of lead deposited and thereby indicates the amount of tetraethyl lead present in the gasoline.

Resistance measurements across the cathode wire segments 120 should be made cautiously. It has been found that the continuous filamentary lead deposit is sensitive to electrical current passing therethrough during measurements. The current tends to alter the shape of the deposit and thereby to increase its resistance. Therefore, quick, periodic measurements are preferred. It is also preferred to employ an ohm meter 134 which requires a very low current.

The principal advantage of detector 100 lies in determining when the quantity of tetraalkyl lead compounds in the gasoline has exceeded a predetermined amount. The amount of lead required to form a continuous deposit depends upon the surface area of the exposed zinc ends and the distance therebetween. These parameters may be adjusted so that a predetermined amount of lead is required to form a continuous deposit and lower the resistance to a desired low value, such as a value of less than 1000 ohms. Thus, a low resistance value indicates that at least the predetermined amount of lead has been extracted and deposited, which amount corresponds to an undesirably high amount of tetraalkyl lead compounds in the gasoline.

Continuous detection within a gasoline tank causes lead to be electrodeposited not only during vehicle operation, but also during periods when the vehicle is parked or inactive. In order that the lead deposit correspond more closely to actual gasoline usage, it is preferred that deposition occur only during vehicle use. This is conveniently accomplished by applying the lead-depositing voltage in detector 100 only concurrently with vehicle use. However, the lead deposit tends to fade or redissolve when no potential is applied. Although the lead quickly redeposits when the potential is reapplied, quick redeposition alters the form of the deposit and thereby affects the resistance measurements. Application of a small potential of less than 1.7 volts and preferably about 0.75 volts to the electrodes during periods of vehicle nonuse deters fading, but is insufficient to deposit additional lead. The resulting deposit more accurately reflects the gasoline usage of the vehicle without being unduly influenced by the contents of the gasoline tank when the vehicle is inactive.

In the preferred embodiments, stainless steel anodes were employed. When lead deposition was carried out using an applied voltage of about 2.0 volts, no visible change or reaction was observed at the anode. The precise nature of the anodic half-cell reaction is uncertain, but is believed to involve oxygen evolution. When the applied potential is greater than about 3.0 volts, visual gassing occurs at the anode, which undesirably depletes the electrolyte solution. Also when the anode consists of an oxidizable metal, such as mild steel, an oxide coating forms at the surface when the preferred 2.0 volts is applied. Thus, the anode is preferably composed of an oxygen resistant material. Besides the preferred stainless steel, suitable anode materials include carbon and platinum. In the preferred embodiments, a potential of at least about 1.7 volts is necessary to deposit lead.

It has been found that lead deposited onto a zinc surface forms a coarse coating comprising dendritic or filamentary crystals. The color of the deposit depends upon its thickness and may vary from a light brownish gray for light coatings to a very dark gray for thick coatings. A cathode composed of zinc initially having a smooth, shiny surface, is preferred for detectors providing visual determination, since the lead deposit may be readily distinguished from the substrate. Suitable lead deposits have also been formed on other metal surfaces, such as nickel or stainless steel, but are generally smoother, denser and not as readily distinguishable. A smooth lead deposit is also significantly more difficult to detect electrically by a device employing a cathode comprising aligned wire segments because a significantly greater lead accumulation is required to form a continuous deposit between segments. In addition, zinc may have a catalytic effect upon lead electrodeposition. Ethylene bromide, another typical gasoline constituent, is also believed extracted into the methanol solution. The zinc surface may catalyze the decomposition of ethylene bromide, forming bromide ions that facilitate lead reduction.

A methanol-based electrolyte solution is preferred because it is capable of extracting tetraalkyl lead from gasoline, but is rendered substantially immiscible in gasoline by the presence of a suitable amount of water. Water-containing methanol is denser than gasoline, readily forming the lower phase of an electrolyte-gasoline system. As little as 0.01 ml. water per 50 ml. methanol is generally sufficient to prevent the methanol from dissolving. This small amount is generally exceeded because significant quantities of water present in commercially available gasoline are extracted into the methanol. In appropriate circumstances, it may be unnecessary to initially add water, since water from the gasoline will prevent methanol dissolution. Another suitable solvent is ethanol, although ethanol is slightly more soluble in gasoline. The preferred electrolyte also contains between 0.25 and 2.5 weight percent KOH. It is apparent that similar quantities of other hydroxide salts, such as NaOH, may be substituted.

Besides the gasoline tetraalkyl lead concentration, several factors affect the ability of the detection method of this invention to extract and deposit lead. In the preferred embodiments, only a small proportion of the tetraalkyl lead is extracted, leaving the gasoline composition and its fuel quality substantially unaffected. The deposition rate is increased by mixing to improve the gasoline-electrolyte contact, increasing the applied potential and increasing the electrolyte conductivity (increasing the KOH concentration). The geometry of the electrode arrangement, including the electrode size and interelectrode distance, also greatly influence the deposition rate. Gravimetric or other analytical techniques may be employed to more accurately measure the lead deposit. Thus, this method may be adapted for laboratory analysis. However, a principal advantage of this detection method is that it may be carried out on board an automotive vehicle under much less carefully controlled conditions.

The method of this invention is also readily adapted to detecting the presence of MMT in gasoline. MMT is readily extracted by the $KOH/H_2O$/methanol electrolyte and manganese is deposited onto the cathode. The manganese deposit formed on a zinc cathode is substantially identical in appearance to that formed by lead, for equivalent atomic metal concentrations. That is, the manganese deposit for gasoline containing a typical MMT concentration of about 0.016 g.Mn per l appears similar to the lead deposit for gasoline containing about 0.063 g Pb per l.

Although this invention has been described in terms of certain embodiments thereof, it is not intended that it be limited to the above description but rather only to the extent set forth in the claims that follow.

The embodiments of the invention in which an exclusive property or privilege is claimed are defined as follows:

1. A method for detecting the presence of a lead or manganese organometallic compound in an automotive gasoline sample, said method comprising assembling an electrochemical cell comprising an anode, a cathode spaced apart from the anode, and an electrolyte contacting the anode and the cathode, said electrolyte comprising water, a soluble inorganic hydroxide and an alcohol taken from the group consisting of methanol, ethanol and mixtures thereof, said electrolyte being substantially immiscible with gasoline, but capable of extracting said organometallic compounds from gasoline containing said compounds, contacting the sample with the electrolyte and thereby extracting said organometallic compound into said electrolyte, applying an electrical potential to the anode and cathode, said potential being suitable to deposit the metallic constituent of said compound onto said cathode, and determining the presence of said metallic deposit on the cathode.

2. A method for detecting the presence of an organometallic compound comprising tetraalkyl lead compound or methylcyclopentadienyl manganese tricarbonyl compound in an automotive gasoline sample, said method comprising placing at least a portion of the gasoline in liquid-liquid extraction contact with an electrolyte portion of an electrochemical cell comprising an anode and a zinc cathode spaced apart from each other and immersed in the electrolyte, said electrolyte comprising methanol, water and a dissolved inorganic hydroxide, said electrolyte being immiscible in said gasoline whereby said organometallic compound is extracted into said electrolyte, applying an electrical potential to the anode and the cathode to deposit the metallic constituent of said compound onto the cathode, and determining the presence of said metallic deposit on the cathode.

3. A method of detecting the presence of a tetraalkyl lead compound in an automotive gasoline sample, said method comprising forming an electrochemical cell comprising an anode and a cathode in spaced relationship and immersed in an electrolyte comprising water, a soluble inorganic hydroxide and methanol, said electrolyte being substantially immiscible in gasoline, but capable of extracting said tetraalkyl lead compound from gasoline, contacting at least a portion of the sample with the electrolyte to extract said compound into the electrolyte, applying to the anode and cathode an electrical potential suitable to deposit elemental lead derived from extracted tetraalkyl lead onto the cathode, and determining the presence of a lead deposit on the cathode, the presence of said deposit thereby indicating the presence of the tetraalkyl lead compound in the sample.

4. A method of detecting tetraalkyl lead compounds in an automotive gasoline sample comprising contacting said sample with a methanol electrolyte solution containing between about 0.25 to 2.5 weight percent potassium hydroxide and containing an amount of water sufficient to render the solution substantially immiscible with gasoline, said solution being capable of extracting tetraalkyl lead from gasoline, immersing in the solution a suitable anode and a spaced cathode, said solution, anode and cathode cooperating to form an electrochemical cell, said cathode comprising at least one metallic zinc surface, applying an electrical potential between the cathode and the anode of between about 1.7 and 3.0 volts to deposit metallic lead upon the cathodically biased zinc surface, and inspecting the lead deposit to determine the amount thereof, which amount is related to the amount of tetraalkyl lead in the sample.

5. A method for indicating the presence of a predetermined amount of tetraalkyl lead compounds contained in an automotive gasoline sample, said method comprising contacting the sample with an electrolyte comprising a methanol solution containing between 0.25 and 2.5 weight percent KOH and also containing at least 0.025 weight percent water to render the solution substantially immiscible with the sample, said electrolyte being capable of extracting tetraalkyl lead from the sample, contacting the electrolyte with a suitable anode and a cathode spaced apart therefrom, said cathode comprising at least two zinc surfaces in facing relationship and spaced apart by a predetermined distance, said zinc surfaces being adapted to collect a metallic lead deposit, applying a suitable potential of between about 1.7 to 3.0 volts between the anode and the cathode surfaces to deposit metallic lead onto said cathode zinc surfaces, the amount of said deposit being related to the amount of tetraalkyl lead in the electrolyte, and measuring the electrical resistance between the cathode zinc surfaces, and determining if the value of the measured resistance is less than a predetermined resistance value corresponding to the presence of at least a predetermined amount of said compounds in the sample.

6. An electrochemical device for detecting the presence of an organometallic compound comprising tetraalkyl lead compound or methylcyclopentadienyl manganese tricarbonyl compound in an automotive gasoline sample, said device comprising an electrolyte adaptable to contact said gasoline sample and comprising a hydroxide ion-containing methanol solution, said electrolyte being substantially immiscible with gasoline and capable of extracting the organometallic compound from gasoline, an anode immersed in said electrolyte, a cathode immersed in said electrolyte and spaced apart from said anode, and means for connecting the anode and the cathode to an electrical power source for applying an electrical potential thereto.

7. An electrochemical device for detecting the presence of tetraalkyl lead compounds in an automotive gasoline sample, said device comprising an electrolyte adaptable to contact said gasoline sample and comprising KOH, water and methanol, said electrolyte being substantially immiscible with gasoline, but capable of extracting tetraalkyl lead therefrom, an anode immersed in said electrolyte, a zinc cathode immersed in said electrolyte and spaced apart from said anode, and connector means for applying a desired electrical potential between the anode and the cathode.

8. An electrochemical device for determining the presence of a predetermined amount of tetraalkyl lead in an automotive gasoline sample, said device comprising an electrolyte comprising a methanol solution containing about 0.25 to 2.5 weight percent KOH and containing water in an amount sufficient to render said electrolyte substantially immiscible with gasoline, a stainless steel anode immersed in said electrolyte, and a cathode comprising at least two facing zinc surfaces spaced apart by a predetermined distance, said surfaces being immersed in said electrolyte and spaced apart from said anode.

9. In an automotive vehicle having an engine and a supply of gasoline for operating said engine, an electrochemical device for monitoring the gasoline composition to detect the presence of a predetermined amount of tetraalkyl lead in said supply, said device comprising an immiscible electrolyte in contact with said supply and comprising a methanol solution containing about 0.25 and 2.5 weight percent KOH, a stainless steel anode in contact with said electrolyte, a cathode assembly comprising two aligned segments of insulated zinc wire each having a central zinc strand and a substantially planar end comprising a surface of said zinc strand, said zinc end surfaces lying immersed in the electrolyte in facing, substantially parallel relationship spaced apart from each other, means for applying an electrical potential between the anode and the cathode zinc end surfaces, and means for measuring the electrical resistance between said zinc end surfaces.

* * * * *